May 15, 1962 C. W. WALTER Re. 25,171

BLOOD ADMINISTERING APPARATUS

Original Filed March 29, 1954 2 Sheets-Sheet 1

Inventor:
Carl W. Walter,
By Emery, Booth, Townsend, Miller & Weidner
Attys

May 15, 1962 C. W. WALTER Re. 25,171

BLOOD ADMINISTERING APPARATUS

Original Filed March 29, 1954 2 Sheets-Sheet 2

Inventor:
Carl W. Walter,
By Emery, Booth, Townsend, Miller & Weidner
Attys

United States Patent Office

Re. 25,171
Reissued May 15, 1962

25,171

BLOOD ADMINISTERING APPARATUS

Carl W. Walter, 191 Highland St., Holliston, Mass.

Original No. 3,004,536, dated Oct. 17, 1961, Ser. No. 419,497, Mar. 29, 1954. Application for reissue Dec. 11, 1961, Ser. No. 160,397
19 Claims. (Cl. 128—214)

Matter enclosed in heavy brackets [ ] appears in the original patent but forms no part of this reissue specification; matter printed in italics indicates the additions made by reissue.

This invention relates to the handling and administering of blood and more particularly to an improved apparatus and method for the sterile, hermetic sealed, clot-free infusion of whole blood. The invention provides a compact, unitary, lightweight, flexible, all plastic apparatus which lends itself to a simple, sure and bacteriologically safe technique with minimum chance of contamination and without danger of air embolism.

The invention will be better understood from a consideration of the following description taken in conjunction with the accompanying drawing in which.

Primary objectives in the administration or infusion of human whole blood to a patient or a recipient are the filtering, detecting and regulating of the blood flow; the exhaustion and exclusion of air from the administering system prior to and during infusion and the provision of a fluid channel which is chemically inert, hemo-repellent, and sealed against contamination from any source. The apparatus and method of this invention are uniquely adapted to these requirements.

This application is a continuation in part of my co-pending application, Serial No. 174,891, filed July 20, 1950, now Patent No. 2,702,034.

Figure 1:
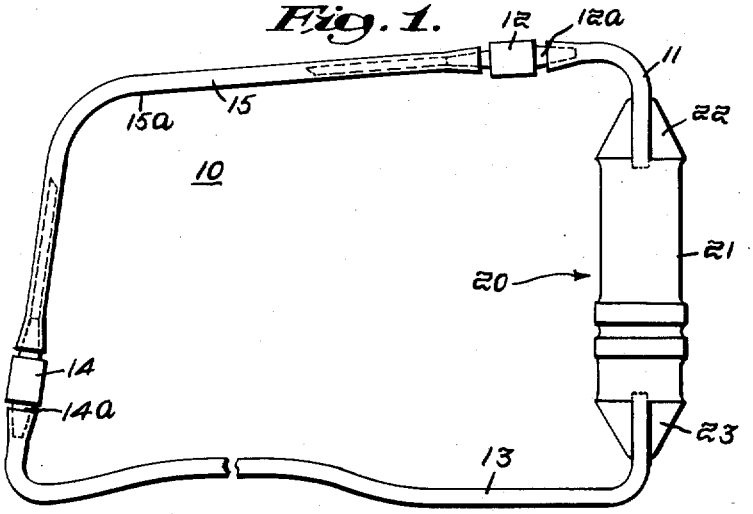
FIG. 1 shows a recipient set according to the invention.
Figure 2:
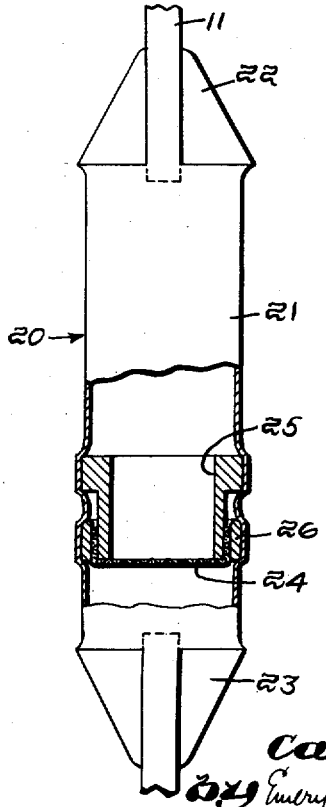
FIG. 2 is a larger scale view of the combination filter drip chamber of FIG. 1.

Referring now more particularly to FIGS. 1 and 2, one form of my novel recipient set is there shown to comprise the fluid or blood conducting assembly 10 and incorporated therein a combination filter and drip column or chamber 20. In accordance with the invention the blood conducting assembly 10, the filter and drip chamber 20, and the blood contacting elements comprised therein are fashioned of a flexible, lightweight plastic of the polyvinyl chloride group having suitable strength and toughness and being impermeable, sterilizable, heat sealable and also inert and hemo-repellent.

The blood conducting assembly 10 comprises more particularly a length 11 of flexible plastic tubing of, say, 3 mm. lumen and 0.5 mm. wall gauge, and of a relatively short length. The outer or free end of the tubing 11 is sized over the hub 12a of a coupling needle 12 such as the preferred illustrated double cone-form as in said parent application or as already known to the art. The other end of the tube 11 is integrally connected at one end 22 of the combination filter and drip chamber 20. At the other end 23 is installed a length 13 of tubing appropriate to infusing purposes, say 3 to 4 feet. The outer or free end of the tubing 13 is seized over the hub 14a of a phlebotomy or infusing needle 14, such as shown and described in my co-pending application above mentioned.

Further in accordance with the invention, the combination filter drip column or chamber 20 comprises a sleeve or short length of larger diameter plastic tubing 21, collapsed and heat sealed at its ends 22, 23. The fusion of the said ends 22, 23 is seen to be accomplished with the ends of the tubes 11, 13 already installed. As in said parent application the relatively larger tubing 21 of the chamber element 20 is similar in composition to that of the smaller tubing 11, 13 and in forming the flat-seal end closures 22, 23 the wall of the larger tubing is brought together upon itself and around the lumen-presenting smaller tubing lengths 11, 13 under externally applied compression.

In the chamber 20 defined in and by the larger-diameter plastic tubing 21, and somewhat nearer the outlet end in the example of FIGS. 1 and 2 is installed a filter screen, which may comprise a nylon bolting cloth 24, FIG. 2, conveniently of 100 mesh and stretched taut across an inner supporting hoop 25, and clamped circumferentially under a concentric, close-fitting outer hoop 26. The hoops 25, 26 are of substantial rigidity and preferably are formed of molded nylon.

For sterile preservation prior to use the pointed ends of the piercing coupler needle 12 and of the infusing needle 14 of the recipient set may be inserted into the opposite ends of a short length 15 of the described flexible tubing, which ends are seen to be forced up over and seized to the cannula mounting hubs of the respective needles. The tube 15 may be nicked at some intermediate point, as at 15a, to permit escape of air and steam during sterilization.

In placing the apparatus in ready-for-use condition, the recipient set is sterilized in any convenient manner, and generally by the application of heat of at least 120° C. for a continuous period of thirty minutes. Further, a non-wetting, clot-preventing or hemorepellent film is desirably applied to the needle cannulas, and pyrogen-free water is rinsed through the tubing assembly 10 and coupled needles 12, 14.

At the time of an infusion, the coupling needle 12 is withdrawn from the sheathing tube 15 and applied to a suitable source, which may be a flexible plastic layflat blood bag such as that described in my co-pending application. The infusing needle 14 will then be applied to the recipient and the blood allowed to flow, the rate being observed at the drip chamber 20. The flow may be induced by gravity, as where the blood source or supply is supported above the level of the patient. Or the infusion may be under squeezing pressure or the like applied to the source of supply, or blood bag.

Figure 3:
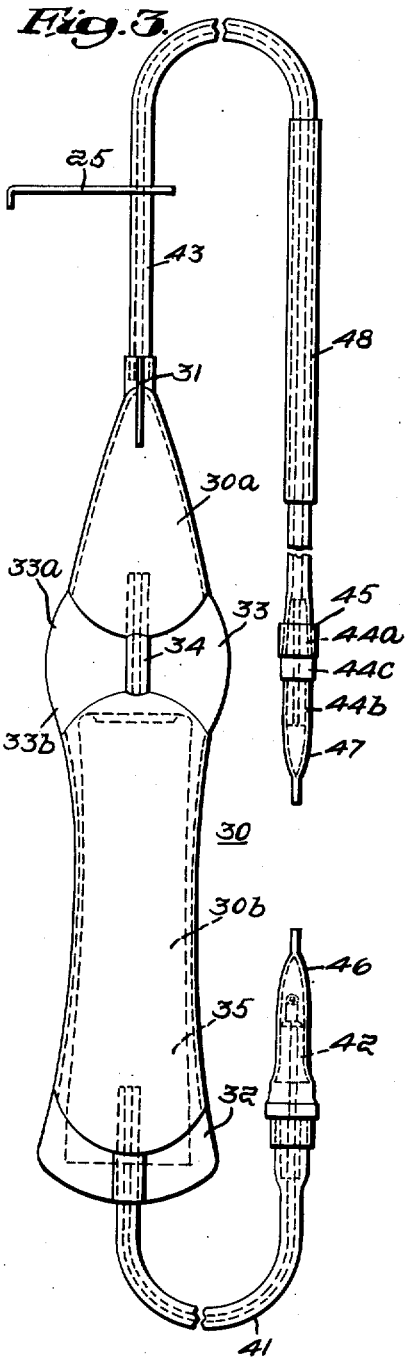
FIG. 3 shows a modified form of the invention apparatus.
Figure 4:
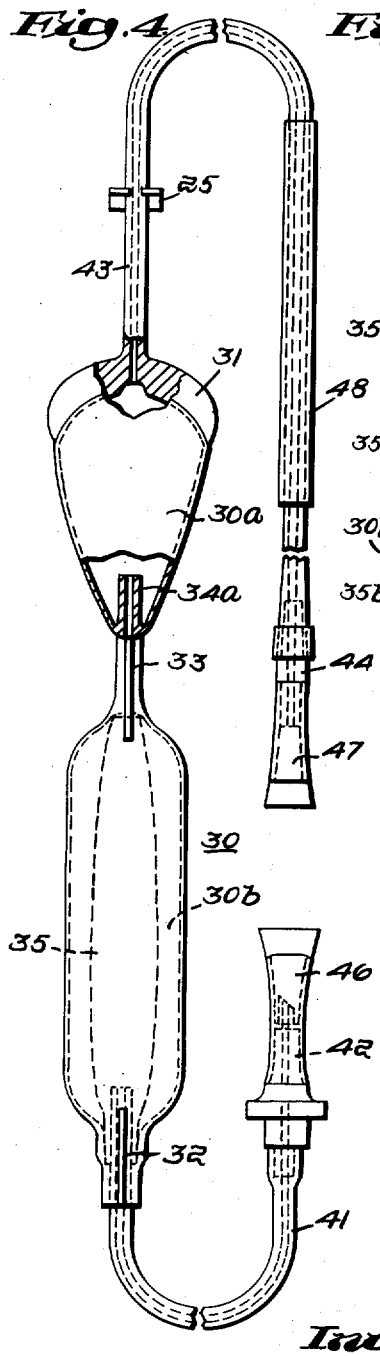
FIG. 4 is a view partly in section and at right angles to FIG. 3.
Figure 5:
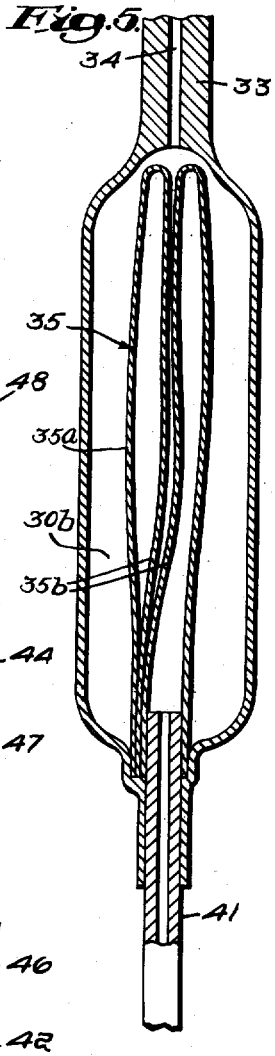
FIG. 5 is a larger scale sectional view of the filter of FIG. 3.

Another and preferred form of the apparatus is illustrated in FIGS. 3 to 5, and there shown centrally to comprise a cylindrical sleeve similarly formed of the disclosed synthetic plastic tubing of the examples of FIGS. 1 and 2 and fitted as a combination filter and drip chamber 30. This modified chamber 30 is formed more particularly of a sleeve flattened and fused together at the ends or margins 31, 32, and also in an intermediate zone 33. In other words, the opposite walls of the ends and the indicated intermediate portion of the tubing or sleeve are collapsed or brought together and dielectrically or heat sealed to define lateral band seals or closures 31, 32, 33, which are seen to be convex, and to define the maximum sleeve width. The intermediate, partitioning seal or closure 33 is shown more particularly to comprise duplicate opposed band seals 33a, 33b. In accordance with the invention, the intermediate seal 33 is relatively closely spaced to one end seal 31, and projects laterally at right angles thereto, FIGS. 3 and 4. Thus the sleeve 30 is formed at one end as a relatively small, i.e. shorter, relatively rigid drip chamber 30a and at the other as a relatively large, i.e. longer, filter chamber 30b. Passage of the blood between the filter and drip chambers 30b, 30a, is effected through a communicating tube 34, which may have a drip forming projection 34a, FIG. 4.

Further in accordance with the invention, filter chamber 30b mounts a filter screen comprising a hemorepellent nylon mesh sleeve inverted or folded back upon itself to define a cylindrical, double-walled envelope. Said envelope is contracted and fused at its open end and between its inner and outer walls 35a, 35b about the end of the collecting tube 41 projecting within the filter chamber 30b.

The preferred form of my novel recipient set is provided similarly as the embodiment of FIGS. 1 and 2 with means for coupling or connection to a blood source, supply or container and for flowing the blood to the filter chamber 30b. Such connecting means may comprise a short, flexible, plastic inlet or collecting tube 41 integrally joined at one end to the sleeve end 32 and seized at the other end to the hub of a coupling needle 42. Alternatively, and to minimize clotting of the blood, the inlet tube may be dispensed with, and the coupler itself received in the sleeve end.

A delivery or infusing tube 43 is coupled similarly as the collecting tube 41 at the other sleeve end 31 and to the drip chamber 30a. The plastic blood administering tube 43 may be of greater length than collecting tube 41, and may carry a phlebotomy needle of known construction. Or it may mount a coupler member 44, FIGS. 3, 5, comprising opposed hubs 44a, 44b tapering oppositely from an enlarged intermediate manipulating portion 44c. The end of the tube 43 is seen to be seized over the one hub 44a and may be fixed thereon by a similarly tapering ferrule or clamping ring 45.

Further in accordance with the invention, the coupling and phlebotomy needles 42, 44, are sealingly encased in sheaths 46, 47, comprising short lengths of the plastic tubing fused at one end and seized at the other over the respective cannulas.

My novel recipient set in the improved embodiment of FIGS. 3 to 5 is sterilized similarly as the FIGS. 1 and 2 form prior to use and as facilitated by the venting mentioned. It will be understood that both forms may be stored and transported in collapsed or folded, sterile-sealed condition.

Considering now the simple, certain infusion technique of the invention in more detail, the inlet tube sheath is first withdrawn and the coupler 42 applied to a blood source as already described. The filter chamber 30b is then squeezed and released to establish a half-way blood level in the same. The phlebotomy needle or adaptor sheath is next removed and the blood flowed through the tube 34, drip chamber 30a and delivery tube 43 to remove the air therefrom. It will be observed that no milking or thumping of the assembly is required. The phlebotomy needle or coupler 44 is then applied to the patient. The rate of flow may be observed at the drip forming projection 34a, and may be regulated as desired by control clip arranged to clamp the outlet tube 43. The flow of the blood may be induced by gravity or by pressure, as mentioned earlier. Additional infusion may be accomplished through a rubber sleeve 48, FIGS. 3 and 4, fitting snugly about a portion of the delivery tube 43. While both concentric sleeves are pierced for the introduction of the added solution, the system seal is preserved when the solution introducing needle is withdrawn by the resilient or elastic closing action of the rubber sleeve 48.

From the foregoing it will be appreciated that I have provided a flexible, lightweight and durable apparatus for the sterile, hermetic-sealed administering of human whole blood. The apparatus has been shown also to be hemo-repellent, to promote free and well-regulated flow, and to lend itself to a simple, certain and biologically safe administering technique, obviously applicable as well to the handling of therapeutic fluids other than plasma and blood, as also disclosed in my prior co-pending application.

It will be understood that my invention, either as to means or method is not limited to the exemplary embodiments or steps herein illustrated or described, and I set forth its scope in my following claims.

I claim:

1. Therapeutic fluid conducting and infusing apparatus comprising a flexible impermeable hemorepellent tube, coupler and needle means at the opposite tube ends, a flexible impermeable hemorepellent sheath sealing said means, and normally sealed apparatus-venting means on said sheath.

2. An integral recipient set for use in a blood and other therapeutic fluid handling system comprising an infusing tube, intermediate chamber-forming enlargement means in the tube, drip-forming and filter means arranged in said enlargement means, coupler and adapter needles mounted at the ends of said tube, and sheath-forming means received on said coupler and adapter needles and sealing said set.

3. A flexible conduit device for sterile administering of blood or other therapeutic fluid from a supply, comprising a tubing assembly including inlet and outlet lengths of flexible elastic transparent normally open-lumen synthetic plastic tubing of a relatively small diameter selected as appropriate for therapeutic fluid conduct, a length of similarly constituted synthetic plastic tubing of relatively larger diameter to present a hollow-chamber-forming enlargement in the tubing assembly between and flow-wise spacing the inlet and outlet tubing lengths with the adjacent open-lumen ends of the latter extending into the respective ends of the enlargement, flat-sealed closures of the ends of said larger diameter tubing, said closures sealingly joined to the ends of said small tubing lengths with said ends embedded in and extending through them as ports into and from the hollow-chambered interior of the enlargement, and filter means and drip-forming means in the flow path in the enlargement, the distal ends of the inlet and outlet tubing lengths being adapted for coupling respectively to a fluid supply and to an infusing needle.

4. Apparatus for conducting and infusing blood or other therapeutic fluids from a supply, comprising a flexible [imperable] *impermeable* hemorepellent synthetic plastic tube, the opposite tube end portions being of selected relatively small diameter adapted for coupler and needle connection, and linearly between said portions a transparent synthetic plastic tubing member of larger diameter having flat sealed ends through which the proximate ends of the tube end portions extend as inlet and outlet ports.

5. Apparatus for conducting and infusing blood and other therapeutic fluids from a supply, comprising a flexible, impermeable, hemorepellent, transparent synthetic plastic tubing assembly including end tubings of relatively small diameter, an intermediate relatively larger chamber-forming tube member of the like composition and terminally defined by flat-seals of the tubing wall material and having the adjacent ends of the end tubings extending openly through them, and means in said chamber-forming member providing a drip-flow formation whereby the rate of the fluid flow through the apparatus may be detected.

6. Apparatus according to claim 5 including filter means in said chamber-forming tubing member.

7. Apparatus for administering whole blood or other therapeutic fluids from a supply, comprising a flexible delivery tube of synthetic plastic composition, coupler and infusing means at the opposite ends of the tube, sheath means detachably sealing said coupler and infusing means, the delivery tube including at a position between the coupler and a point spaced from the infusing means a length of flexible synthetic plastic tubing of larger diameter than the rest of said delivery tube so as to present a chamber-forming enlargement in and having its ends in sealed flow communication with preceding and following portions of said tube, and drip-forming and filter means in said enlargement.

8. Apparatus for administering blood and therapeutic fluids from a supply, comprising a length of flexible elastic transparent tubing of impermeable inert hemorepellent plastic material presenting a filter-containing and drip-flow-providing hollow chamber formation integrally formed of and by the tubing and terminally defined by longitudinally spaced transverse flat seals of the tubing wall and chamber inlet and outlet means extending longitudinally through the seals.

9. Apparatus for administering therapeutic fluids from a supply, comprising a fluid flow conduit device formed of a length of flexible elastic transparent thermoplastic tubing flattened and integrally fused at axially spaced transverse sealing zones each of which has a reduced longitudinal port therethrough, the port of one sealing zone providing a fluid inlet to the device, the port of another sealing zone providing a fluid outlet from the device, the tubing wall of the device providing between such sealing zones a normally open tubular chamber formation presenting a viewable flow path therethrough, said transverse sealing zones being formed each in a plane extending substantially diametrically of the tubing and in determined orientation with respect to one another, and said chamber formation housing a drip-flow forming means in the flow path therein.

*10. Equipment for conducting and infusing fluid from a supply having an outlet comprising a line of tubing of flexible impermeable transparent plastic non-wettable to blood and with the opposite ends connectible to the supply outlet and to an infusing needle, an intermediate tubular chamber-forming enlargement in the tubing, and filter means and drip-forming means in said enlargement, the latter presenting a wall through which the rate of drip flow may be observed.*

*11. An infusing assembly adapted to be coupled to a storage vessel for conducting blood therefrom, comprising a flexible impermeable infusing tube non-wettable to blood, coupling and infusing needles in sealed connection to the opposite ends of the tube, said infusing tube having at an intermediate location a chamber-forming enlargement into which the smaller-diametered tube extends sufficiently to provide a drip-forming inlet, the enlargement defining a drip chamber permitting observation of the rate of blood flow.*

*12. An infusing assembly according to claim 11 wherein the drip chamber has mounted in the flow path therein a fine mesh screen of a material non-wettable to blood.*

*13. For use in fluid infusion, a flow chamber unit comprising a tubular element of a flexible transparent plastic non-wettable to blood and defining a hollow chambered body with inlet and outlet ends, said body having at the respective ends opposed terminal wall structure longitudinally and transversely disposed thereon to provide body end closure means at said ends, one said end closure means equipped with a fluid inletting tubular coupling for connection to a fluid supply container and the other end having tubular outletting connection for flow to an infusing needle, and drip forming means in the flow path in said chambered body.*

*14. For use in fluid infusion, a flow chamber unit comprising a tubular element of a flexible transparent plastic non-wettable to blood and defining a hollow chambered body with inlet and outlet ends, said body having at the respective ends opposed terminal wall structure longitudinally and transversely disposed thereon to provide body end closure means at said ends, one said end closure means equipped with a fluid inletting tubular coupling for connection to a fluid supply container and the other end having tubular outletting connection for flow to an infusing needle, and means defining a port in the flow-path in said body spaced for fall of fluid thereat for flow-rate observation purposes.*

*15. For use in fluid infusion, a flow chamber unit comprising a tubular element of a flexible transparent plastic non-wettable to blood and defining a hollow chambered body with inlet and outlet ends, said body having at the respective ends opposed terminal wall structure longitudinally and transversely disposed thereon to provide body end closure means at said ends, one said end closure means equipped with a fluid inletting tubular coupling means for connection to a fluid supply container and the other end having tubular outletting connection for flow to an infusing needle, and drip and filter means in the flow path in said body.*

*16. For use in fluid infusion, a flow chamber unit comprising a tubular element of a flexible transparent plastic non-wettable to blood and defining a hollow chambered body with inlet and outlet ends, said body having at the respective ends opposed terminal wall structure longitudinally and transversely disposed thereon to provide body end closure means at said ends, one said end closure means equipped with a fluid inletting tubular coupling for connection to a fluid supply container and the other end having tubular outletting connection for flow to an infusing needle, means defining a port in the flow-path in said body spaced for fall of fluid thereat for flow-rate observation purposes, said body also containing filter means in the flow-path therein.*

*17. In a recipient set for infusing fluids from a fluid container, a fluid-administering length of flexible and elastic plastic tubing with one end connectible to an infusing needle, a larger-diametered section of flexible plastic tubing non-wettable to blood and defining a hollow chambered body with inlet and outlet ends each having a closure thereat, said body outlet end connected through the closure thereat to the end of said first mentioned tubing distal to the infusing needle, relatively short tubular inlet means extending through the other end closure of said chambered body and including a relatively stiff terminal element for connection to a fluid container, and drip forming means in the flow path in said chambered body, said body being substantially transparent for observation of fluid level and flow rate therein.*

*18. In a recipient infusing device for administering fluids, a tubular chambered body of a flexible plastic non-wettable to blood, said body having at the respective ends opposed terminal wall structure longitudinally and transversely disposed thereon to provide end closure means at each end of the body, each with a through passage, a tubular inlet means extending from the body interior through one closure means and projecting for connection to a fluid container, and tubular outlet means extending from the body interior through the other end closure means, the body being substantially transparent for observation of flow rate therein and containing filter and drip means in the path of flow.*

*19. An infusing assembly adapted to be coupled to a storage vessel for conducting therapeutic fluid therefrom, comprising a through-flow tubular infusion line having between the ends thereof a relatively enlarged diameter tubular section being transparent flexible impermeable and non-wettable to blood and defining a view chamber with inlet and outlet ends connected into the line, said tubular infusion line comprising also a flexible impermeable smaller diametered tubing length leading from the chamber outlet end for delivery of the fluid, and a tubular coupling element of similar relatively small diameter at the chamber inlet end and extending internally into the chamber sufficiently to provide a drip-forming inlet port for observation of the rate of flow within the chamber, at least an external terminal portion of said tubular*

*coupling element comprising a coupling needle for plug-in connection to a fluid storage vessel.*

References Cited in the file of this patent or the original patent

UNITED STATES PATENTS

| | | |
|---|---|---|
| 2,118,893 | Meerbeck | May 31, 1938 |
| 2,186,987 | Nesset | Jan. 16, 1940 |
| 2,322,701 | Nesset et al. | June 22, 1943 |
| 2,341,114 | Novak | Feb. 8, 1944 |
| 2,452,643 | Fields | Nov. 2, 1948 |
| 2,452,644 | Fields | Nov. 2, 1948 |
| 2,461,558 | Meagher | Feb. 15, 1949 |
| 2,470,943 | Page | May 24, 1949 |
| 2,653,606 | Ryan | Sept. 29, 1953 |
| 2,664,085 | Ryan | Dec. 29, 1953 |

| | | |
|---|---|---|
| 2,702,034 | Walter | Feb. 15, 1955 |
| 2,704,544 | Ryan | Mar. 22, 1955 |

FOREIGN PATENTS

| | | |
|---|---|---|
| 165,283 | France | Nov. 10, 1884 |
| 761,528 | France | Jan. 5, 1934 |

OTHER REFERENCES

Walter et al.: "A Closed Gravity Technique for Preservation of Whole Blood in ACD Solution Utilizing Plastic Equipment," Surgery, Gynecology and Obstetrics, vol. 94, June 1952, pages 687–692. (Copy in Scientific Library.)

Fenwall Advertisement—Surgery, Gynecology, and Obstetrics, vol. 95, No. 4, October 1952, page 12 of the advertising section. (Copy in Scientific Library.)